United States Patent
Burgett et al.

(10) Patent No.: US 9,843,855 B2
(45) Date of Patent: *Dec. 12, 2017

(54) IMAGE CAPTURE AND EARPIECE SIZING SYSTEM AND METHOD

(71) Applicant: HARMAN INTERNATIONAL INDUSTRIES, INC., Stamford, CT (US)

(72) Inventors: Seth Burgett, Glen Carbon, IL (US); Richard J. Daniels, St. Louis, MO (US); Bharat Rajaram, St. Louis, MO (US); Michael D. Wetle, St. Louis, MO (US); Tonya An, Grand Rapids, MI (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,602

(22) Filed: Jun. 5, 2015

(65) Prior Publication Data

US 2015/0271588 A1    Sep. 24, 2015

Related U.S. Application Data

(63) Continuation of application No. 12/985,892, filed on Jan. 6, 2011, now Pat. No. 9,050,029.

(Continued)

(51) Int. Cl.
*H04N 7/18* (2006.01)
*H04R 1/10* (2006.01)
*A61B 5/107* (2006.01)

(52) U.S. Cl.
CPC ......... *H04R 1/1058* (2013.01); *A61B 5/1076* (2013.01); *A61B 5/1079* (2013.01); *H04R 1/1016* (2013.01); *H04R 2201/105* (2013.01)

(58) Field of Classification Search
CPC .................................................. H04R 1/1058

(Continued)

(56) References Cited

U.S. PATENT DOCUMENTS 5,592,248 A    1/1997  Norton et al.
5,603,187 A    2/1997  Merrin et al.

(Continued)

FOREIGN PATENT DOCUMENTS

CN    2435706 Y    6/2001
CN    201401994 Y    2/2010

(Continued)

OTHER PUBLICATIONS

European Search Report for Application No. PCT/US2010/045773 dated Oct. 7, 2010, 9 pages.

(Continued)

*Primary Examiner* — Richard Torrente
(74) *Attorney, Agent, or Firm* — Brooks Kushman, P.C.

(57) ABSTRACT

A method and system for sizing an earpiece include situating a calibration device proximate a user's ear. The user holds an image capture device so as to aim the image capture device at the user's ear. The user then touches and holds a random area of the touch screen display and releases the touch screen display to activate the image capture device and capture an image of the user's ear and the calibration device. The captured image is then analyzed and an earpiece size is determined based on the analysis of the image.

13 Claims, 5 Drawing Sheets

Related U.S. Application Data (60) Provisional application No. 61/292,699, filed on Jan. 6, 2010.

(58) Field of Classification Search
USPC .......................................................... 348/77
See application file for complete search history.

(56) References Cited

U.S. PATENT DOCUMENTS

| | | | |
|---|---|---|---|
| 6,053,931 | A | 4/2000 | Lizcano |
| 6,692,127 | B2 | 2/2004 | Abitbol et al. |
| 8,111,864 | B2 | 2/2012 | Oliveira et al. |
| 2003/0074174 | A1 | 4/2003 | Fu et al. |
| 2004/0004633 | A1 | 1/2004 | Perry et al. |
| 2004/0189935 | A1 | 9/2004 | Warden et al. |
| 2005/0082370 | A1 | 4/2005 | Frantz et al. |
| 2005/0088435 | A1* | 4/2005 | Geng .................... G06T 7/0022 345/419 |
| 2005/0238194 | A1 | 10/2005 | Chomenky |
| 2006/0204013 | A1 | 9/2006 | Hannibal et al. |
| 2007/0036376 | A1 | 2/2007 | Fried |
| 2007/0036383 | A1 | 2/2007 | Romero |
| 2007/0183603 | A1 | 8/2007 | Jin et al. |
| 2008/0013794 | A1 | 1/2008 | Kalker et al. |
| 2009/0041287 | A1 | 2/2009 | Quinlisk |
| 2009/0195678 | A1* | 8/2009 | Zhao .................... G03B 17/12 348/273 |
| 2010/0020221 | A1* | 1/2010 | Tupman .............. G06F 3/04883 348/333.01 |
| 2011/0290005 | A1 | 12/2011 | Hart et al. |

FOREIGN PATENT DOCUMENTS

| | | |
|---|---|---|
| DE | 20304099 U1 | 7/2003 |
| DE | 102005012054 A1 | 9/2006 |
| JP | 2002115374 A | 4/2002 |
| JP | 2003008046 A | 1/2003 |
| JP | 2003184235 A | 7/2003 |
| JP | 2005064147 A | 3/2005 |
| KR | 100915679 B1 | 9/2009 |
| WO | 9012990 A1 | 11/1990 |
| WO | 2009013607 A2 | 1/2009 |
| WO | 2009120923 A2 | 10/2009 |
| WO | 2011014655 A2 | 2/2011 |

OTHER PUBLICATIONS

Extended European Search Report for PCT Application No. PCT/US2010/045773 dated Sep. 23, 2013, 5 pages.
Non-Final Office Action mailed Jun. 10, 2013 in Related U.S. Appl. No. 12/985,892, filed Jan. 6, 2011, 10 pages.
Final Office Action mailed Dec. 24, 2013 in Related U.S. Appl. No. 12/985,892, filed Jan. 6, 2011, 7 pages.
Non-Final Office Action mailed Sep. 16, 2014 in Related U.S. Appl. No. 12/985,892, filed Jan. 6, 2011, 6 pages.
PCT International Search Report, PCT/US2011/045773 (Jul. 3, 2012), 3 pages.

\* cited by examiner

IMAGE CAPTURE AND EARPIECE SIZING SYSTEM AND METHOD

CROSS-REFERENCE TO RELATED APPLICATIONS

This application is a continuation of U.S. application Ser. No. 12/985,892 filed Jan. 6, 2011, published as U.S. Publication No. 2011/0164128, will be issued as U.S. Pat. No. 9,050,029, which, in turn, claims the benefit of U.S. provisional application Ser. No. 61/292,699 filed Jan. 6, 2010, the disclosures of which are hereby incorporated in their entirety by reference herein.

BACKGROUND

Portable music players and portable telephones are becoming increasingly common Owners of these and similar devices often prefer to use them in conjunction with personal sound delivery devices. These devices are worn, for example, while driving (e.g. telephone headset), exercising, traveling, or studying or the like.

Nearly all music players and portable phones have one or more earpieces such as earbuds as a standard accessory, but typical one-size-fits-all earpieces often do not stay in the user's ears or become uncomfortable over time.

Proper fitting earbuds or in custom ear monitors can provide the benefit of ambient noise isolation or suppression similarly to how earplugs block sound. However, stock earbuds often do not fit well enough to accomplish this.

In an attempt to address the above described earbud fit problems some companies offer kits of different size earbud adapters. The user selects, through a process of trial and error, the earbud adapter that fits his ear the best. While the probability of a better fit is thus increased, it is still inadequate because the variation in human ear anatomy is too great to be accommodated with a kit that is necessarily limited in its range of shapes and sizes. Furthermore, this approach requires the user to try on each earbud adapter and determine, sometimes over several hours use, if it provides the best fit. Finally, once the optimal earbud adapter is selected, the remaining ones are useless and this results in material waste. Some companies provide a single flexible or compliant earbud adapter where the user is able to adjust its shape and size and/or the material is able to be compressed and then expand to conform to the inner surfaces of the user's ear anatomy. This flexibility or compliance partially addresses the above mentioned problems with kits, but the extent of the flexibility or compliance is necessarily limited to provide optimal results for a small range of anatomy centered on the average ear. When purchasing this product, the user will typically not know in advance whether his ears will fall within the range of the adapter's accommodation which typically creates areas of pressure on known pain points within the ear.

To solve the above mentioned problems other companies supply full custom earbuds or earbud adapters. They do this by first injecting a soft material into the user's ear to form a physical impression or mold. The mold supplies the ear shape information that is then used to manufacture the custom fitted earbud or earbud adapter. While this full custom approach solves many of the problems outlined above, it requires a significant amount of skilled labor which elevates the production cost. Production costs are further increased because the full custom approach necessarily precludes mass production. Additionally, the user must undergo the molding process which can be uncomfortable, scary and time consuming And finally, the user must wait several business days while the custom solution is built and shipped. In this model, a custom fit earbud may require skilled labor to eliminate pressure points in areas known to be painful within the ear such as the Crus of Helix, the Tragus, the Anti-Tragus and the Anti-Helix.

For these and other reasons, there is a need for the present invention.

SUMMARY

In accordance with aspects of the present disclosure, a method and system for sizing an earpiece include situating a calibration device proximate a user's ear. The user holds an image capture device so as to aim the image capture device at the user's ear. The user then touches and holds a random area of the touch screen display and releases the touch screen display to activate the image capture device and capture an image of the user's ear and the calibration device. The captured image is then analyzed and an earpiece size is determined based on the analysis of the image.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

An earbud herein means a personal sound delivery device that fits substantially within the outer ear and which comprises an acoustic emitter.

An earbud adapter herein means a physical adapter that first, physically and acoustically connects to an earbud and second; physically and acoustically connects to the user's ear. An earbud adapter does not include an acoustic emitter.

An in ear monitor herein means a physical ear adapter that first, physically and acoustically contains an acoustic emitter and second; physically and acoustically connects to the user's ear through a contoured form to fit a single individual's ear. An in ear monitor contains an acoustic emitter that permanently or semi-permanently attaches an acoustic emitter and ear adapter.

An earpiece generically refers to devices such as earbuds, earbud adapters, in ear monitors, etc.

This disclosure concerns a system and method that enables self-portrait image capture, which can be included as part of a method of sizing for personalized earpieces. In some implementations, the system and method are embodied as operating on an Apple iPhone with Apple iPhone-specific software and protocols. For the sake of simplicity, the present disclosure is presented in terms of an Apple iPhone and associated applications ("Apps"). However, it is understood that other embodiments are envisioned where the system and method are implemented using other platforms and devices.

Advantages of embodiments of the system and methods disclosed herein include

Integration: The iPhone is equipped with a camera, web-browsing and third-party applications to combine all components of the Custom-Fit Earbud Enhancer system into one: digital image capture, size determination and online ordering. The software application enables self-photography.

Lower cost: The built-in camera on the iPhone makes taking digital images free and instant. The standard fees for web-browsing and email service may apply. Consumers have the convenience and power of taking their own ear image, thereby eliminating the costs of sizing service and fitting centers.

Convenience: The user may easily take an image of his own ear without the help of others. Once a user has taken the image, the application coordinates email of the photo attachment to the sizing server. The user promptly receives a response message consisting of the personal earbud enhancer size on his iPhone and order options.

High prevalence: The popularity of the Apple iPhone enables many users to take advantage of the camera feature for earbud enhancer sizing. Downloading specialized applications is fast and easy. The portability of the mobile phone camera allows for application download and image capture at any time or location.

Improved usability: The existing procedure for iPhone photography requires a user to stand physically behind the phone while pointing the camera at the desired object. Pressing a shutter icon on the touch screen will capture the photo. Self-photography is challenging because of the indistinct shutter button.

Security and privacy: The security encryption of the iPhone and sizing server allows maximal protection of the users sizing and personal information. Self-photography also protects the user's privacy and personal space.

Figure 1A:
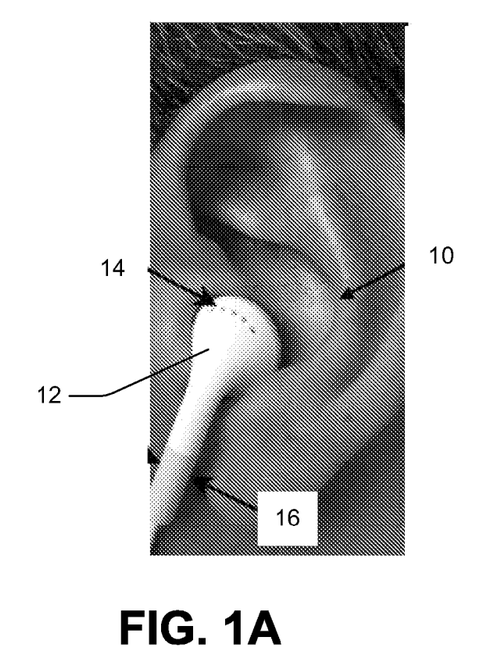
FIGS. 1A and 1B illustrate examples of images of an ear and calibration devices.
Figure 1B:
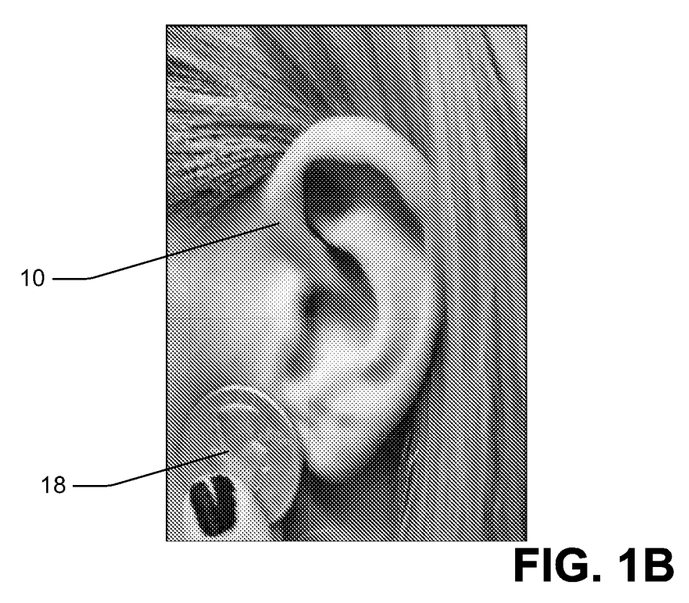

It has been shown that a 2D digital image of the ear enables measurement of a dimension or multiple dimensions of the ear such that an ear prosthetic device such as an earpiece could be sized and fitted for the sample ear. During the image acquisition process, the size of the ear is calibrated to a calibration device—a known object such as a ruler, coin, or an earbud device situated proximate the ear to calibrate the image. FIG. 1A includes an image of an ear 10 with an earbud 12 situated in the ear 10 to function as a calibration device. The earbud 12 itself could function as the calibration device, or various parts of the earbud could perform this function, such as holes 14 in the earbud or the wire or wire connection 16. FIG. 1B shows the ear 10 with a coin 18 held near the ear 10 to function as a calibration device.

The development of a software application for iPhone provides user-controlled image acquisition and self-capture of an acceptable image of the ear.

Figure 2:
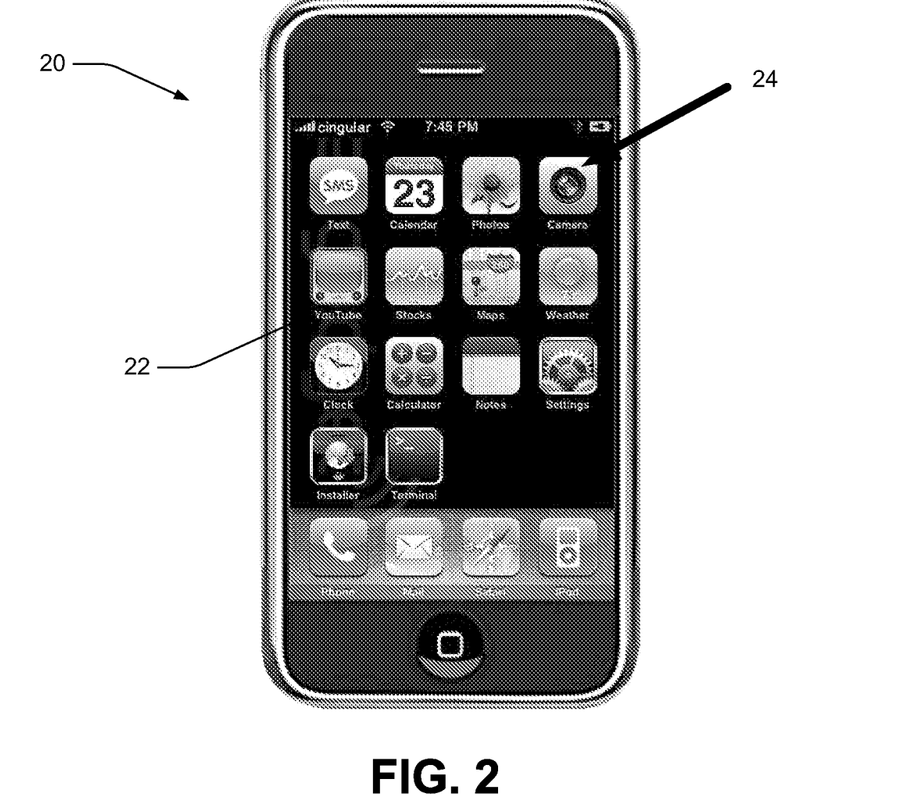
FIG. 2 illustrates an example of a mobile phone.

An example of an iPhone 20 and its display screen 22 are illustrated in FIG. 2. The iPhone features a built-in camera system for digital photography. Accessing the "camera" icon 24 from the main menu automatically starts the camera to digitally display the streaming acquisition on the screen. The iPhone has limited self-focusing capabilities and readjusts the image when one taps on an area of the screen. To take the photo, one must tap the "capture" (gray camera) on the horizontal bar at the bottom of the screen touch screen associated with the camera function. Doing so activates the camera to shoot the image, accompanied by a shutter animation. This design imposes challenges to self-photography because the icon is only an image on the touch screen and not a physical button. Due to the size and position of this icon, one must look at the screen to locate and touch it. The configuration of the system makes the camera snap the photo at the first initial touch on the "capture" icon. Given these limitations, all existing procedures for image acquisition of an ear photo using the iPhone have relied on another individual present to hold and point the iPhone camera and tap the "capture" button. It may be inconvenient to involve another person. Furthermore, the lack of a zoom function on the iPhone causes possible proximity-related discomfort when another is taking close-up images of the ear.

The disclosed system and method interfaces with the phone's camera system hardware. The new configuration settings can generate a different mechanism of image capture. The entire touch screen becomes sensitive and acts as the shutter control. The initial touch no longer activates the camera. Instead, image capture occurs when the touch is released. The application walks the user through the procedure of take a self-image of the ear. For proper sizing, the digital photo of the ear must be in-focus and well-lit. Only one ear is needed for sizing and either ear is acceptable. In certain embodiments, a reference object must be included in the photo to determine the scale of the image. Suitable solutions include a standard apple earbud inserted in the ear, or a ruler or coin held up for reference.

Figure 3:
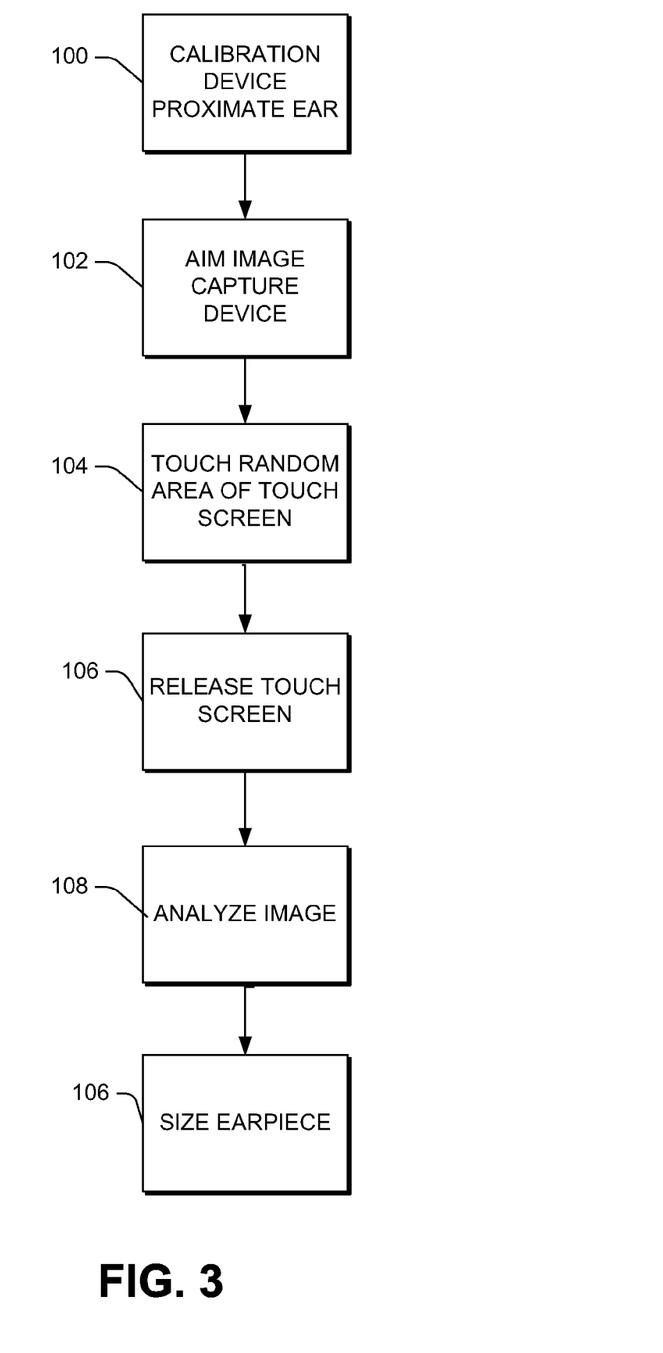
FIG. 3 is a flow diagram illustrating an embodiment of a disclosed method.

FIG. 3 is a flow diagram generally illustrating an example of a disclosed method for sizing an earpiece. In block 100, a calibration device is situated proximate a user's ear. As noted above, an earbud positioned in the ear or a coin situated next to the user's ear are examples of suitable calibration devices. In block 102, the user holds an image capture device, such as an iPhone with the camera function activate, so as to aim the device at the user's ear. In block 104, the user touches and holds a random area of the touch screen display, and in block 106 the user releases the touch screen display to activate the image capture device and capture an image of the user's ear and the calibration device. In block 108 the captured image is analyzed and in block 110 an earpiece size is determined based on the analysis of the image.

The following are sample instructions for a self-photographing procedure in accordance with an example iPhone-based implementation.

1. Place a white Apple earbud in your left ear as normal.
2. Keeping the iPhone vertical, use your left index finger to touch and hold any part of the iPhone screen. The photo will be captured when you release.
3. Extend your arm so that the iPhone is 1-2 ft. away from your left ear.

4. Adjust the angle as necessary so that the camera lens points toward the ear.

5. Release your finger from the screen and remain still for 2 seconds as the camera captures the photo. You may hear the shutter animation sound.

In some implementations, the image capture device has images stored in a memory thereof After the image is acquired, the user can review the captured image and compare it with the stored examples of "acceptable" vs. "incomplete" ear photos. The consumer confirms the satisfactory image to let the application electronically send it to an earpiece sizing server.

Unique to this application is the iPhone camera hardware interface that activates the full screen for image capture. Previously, self-photography was difficult because the user had to hold the iPhone with the screen facing away and randomly tap for the "capture" button. Transforming the entire screen into a shutter control significantly increases the ease of this process, since any random are of the screen can be used to activate the image capture function. In addition, the mechanism for "release capture" is advantageous over tapping the screen. It enables the user to maintain a good grasp of the iPhone and manipulate camera distance and angle. The user does not have to avoid touching the screen when positioning the camera; rather a quick finger release, when the camera is ready, captures the desired image. The design and configuration of this system provides the optimum ease and efficiency for self-photography. The risk of dropping and damaging the iPhone device while performing the procedure is minimized.

In addition to the iPhone camera limitations, the ear is anatomically beyond the range of vision and especially difficult to self-photograph. The functionalities of "full screen activation" and "release capture" of the iPhone image capture application fully support the earbud enhancer sizing protocol to acquire ear images.

The development of this new image capture mechanism is in conjunction with a digital earbud enhancer sizing application. However, the capability of self-photography using the iPhone can apply to a variety of purposes/situations. The functionality can be an application by itself to allow users to easily take images of themselves for self-portraits. The possibility of making this functionality part of the standard Apple iPhone update would make it ubiquitous and accessible to all users.

The following sources (incorporated by reference) provide further information regarding taking photos with an iPhone:

http://www.applelinks.com/index.php/more/how to take better photos with your ip hone/http://www.apple.com/iphone/iphone-3gs/photos.html http://www.iphoneography.com/journal/2009/9/25/new-iphone-photo-app-self-portrait-made-easy.

In some implementations, the mobile phone communication capabilities are used to transmit the captured image to a remote location for the analysis and earpiece sizing determinations. For instance, the image could be sent to an earpiece sizing server via the internet. This also allows for immediate purchase and shipping of the properly sized earpiece to the user.

Figure 4A:
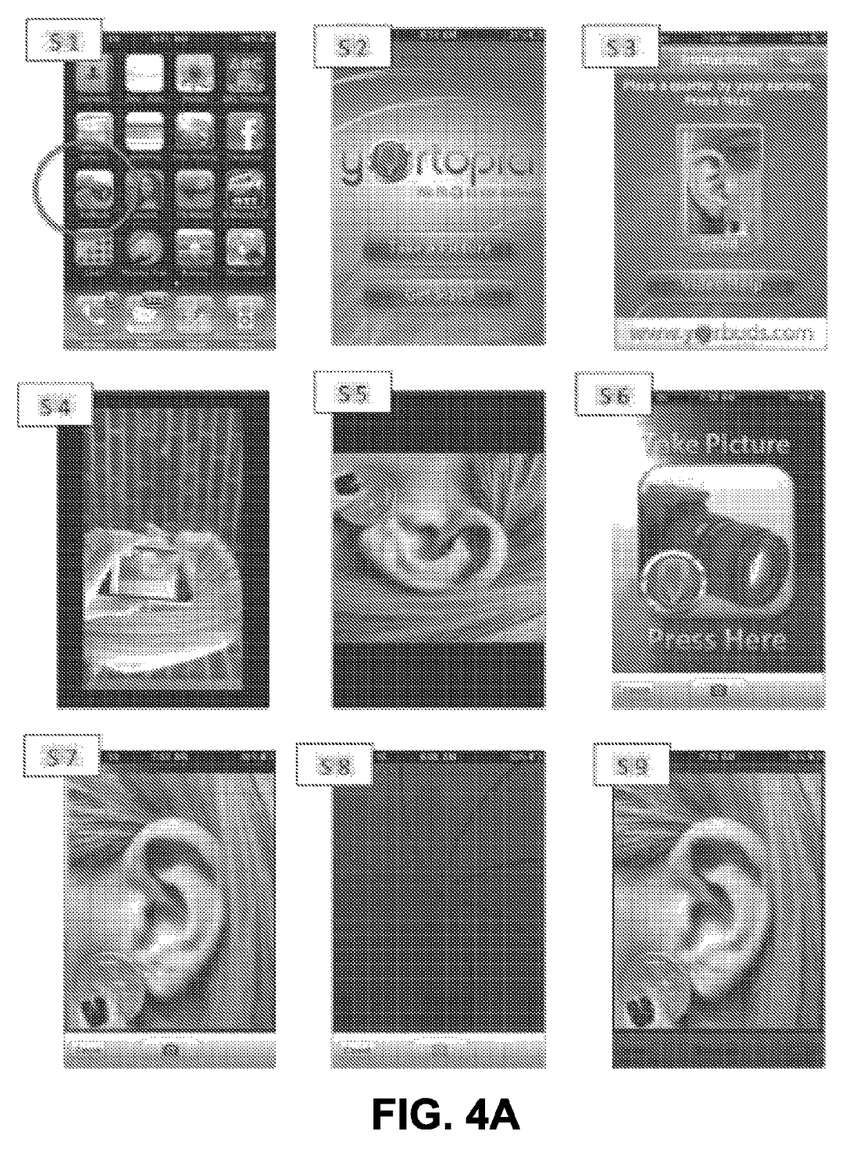
FIGS. 4A and 4B illustrate a series of screen shots associated with an exemplary implementation of a disclosed method.
Figure 4B:
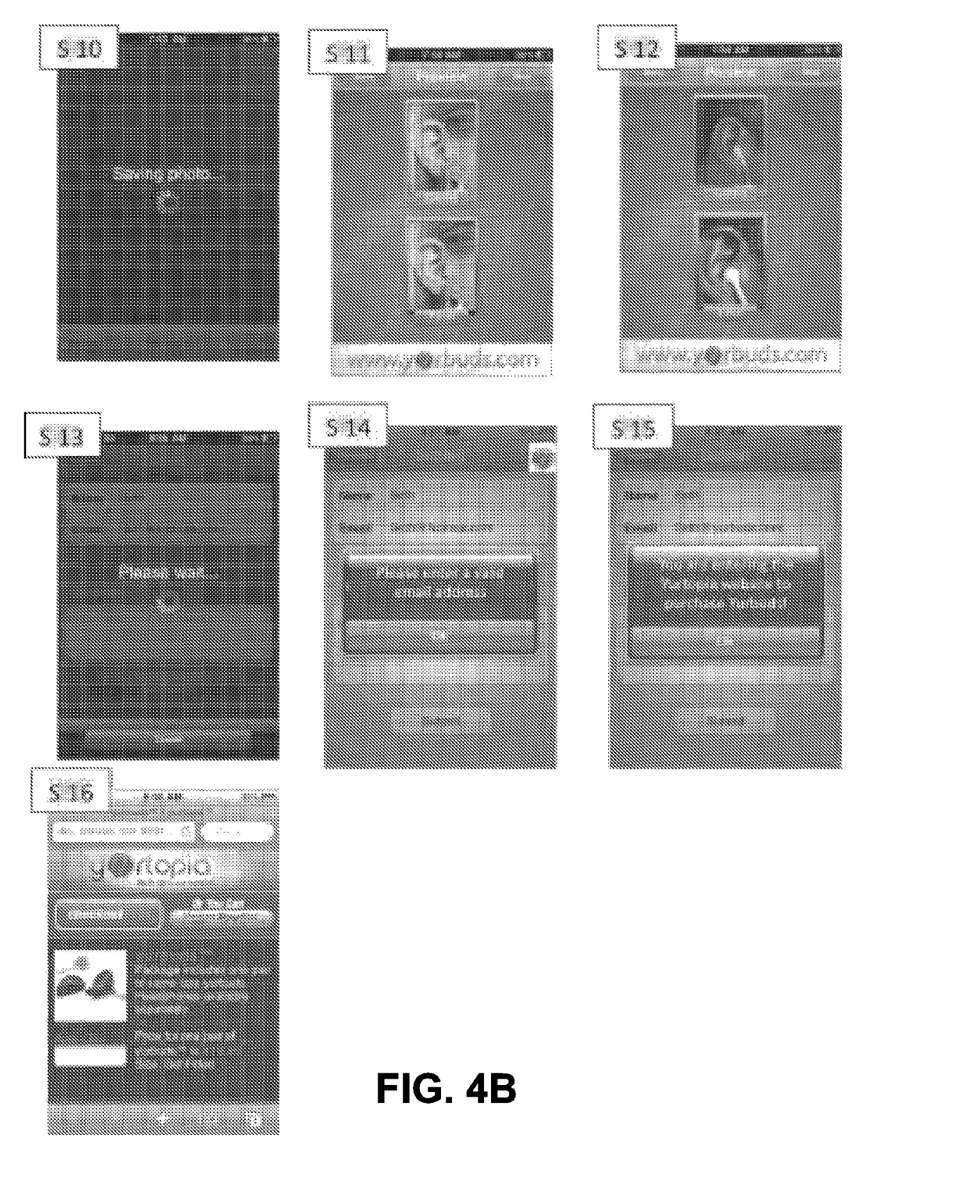

FIGS. 4A and 4B provide corresponding application screen shots S1-S16 for the following description of an example workflow for mobile a device with camera and internet capability, such as an Apple iPhone and associated Application.

Screen 1 (S 1): Application icon to start

S 2: Take a picture as a picture taking tool or Get Sized for earbud adapter.

S 3: Instructions screen with option to view a How To Video or pictorial description.

S 4: Video description of How To.

S 5: Static picture description of How To.

S 6: Splash screen showing that user can touch anywhere on screen—fading away.

S 7: View prior to taking picture.

S 8: Capturing image.

S 9: Preview and retake or Use image.

S 10: Saving a Get Sized photo or standard photo.

S 11: Comparison photo using a Quarter as a reference object.

S 12: Comparison photo using a standard Apple earbud as a reference object.

S 13: Processing a submission with the option to input an Affiliate code or Gift code.

S 14: Error message.

S 15: Notification of transition away from Application and to an e-commerce website to purchase.

S 16: Mobile device website for purchase.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A system for sizing an earpiece, the system comprising:
an image capture device including a touch screen display configured to:
display an image capture screen to provide image capture instructions to a user;
receive a user input at the touch screen display based on the image capture instructions; and
capture an image of an ear of the user along with a calibration device positioned proximate to the ear of the user in response to the input to determine an appropriate earpiece size for the user, wherein the calibration device corresponds to a reference object that includes one of more dimensions.

2. The system of claim 1, wherein the image capture instructions include textual instructions regarding the capturing of the image.

3. The system of claim 1, wherein the image capture instructions include pictorial instructions regarding the capturing of the image.

4. The system of claim 1, wherein the image capture instructions include textual and pictorial instructions regarding placement of the calibration device proximate to the ear of the user.

5. The system of claim 1, wherein the image capture device is further configured to present a predetermined acceptable image to compare to the captured image.

6. The system of claim 1, wherein the image capture device is further configured to provide an option to input a gift code.

7. The system of claim 1, wherein the image capture device is a mobile phone.

8. An image capture device for sizing an ear piece, the image capture device comprising:

a mobile phone including a touch screen display configured to:
    display an image capture screen to provide image capture instructions to a user;
    receive a user input at the touch screen display based on the image capture instructions; and
    capture an image of an ear of the user along with a calibration device positioned proximate to the ear of the user in response to the input to determine an appropriate earpiece size for the user, wherein the calibration device corresponds to a reference object that includes one of more dimensions.

9. The device of claim 8, wherein the image capture instructions include textual instructions regarding the capturing of the image.

10. The device of claim 8, wherein the image capture instructions include pictorial instructions regarding the capturing of the image.

11. The device of claim 8, wherein the image capture instructions include at least one of textual and pictorial instructions regarding placement of the calibration device proximate to the ear of the user.

12. The device of claim 8, wherein the image capture device is further configured to present a predetermined acceptable image to compare to the captured image.

13. The device of claim 8, wherein the image capture device is further configured to provide an option to input a gift code.

* * * * *